United States Patent [19]

Malfroot et al.

[11] Patent Number: 4,614,829

[45] Date of Patent: * Sep. 30, 1986

[54] PROCESS FOR THE PREPARATION OF α-CHLORINATED CHLOROFORMATES

[75] Inventors: Thierry A. Malfroot, Saint-Germain-les-Corbeil; Jean-Pierre G. Senet, La Chapelle la Reine, both of France

[73] Assignee: Societe Nationale des Poudres et Explosifs, Paris, France

[ * ] Notice: The portion of the term of this patent subsequent to Jun. 3, 2003 has been disclaimed.

[21] Appl. No.: 641,602

[22] Filed: Aug. 17, 1984

[30] Foreign Application Priority Data

Aug. 26, 1983 [FR] France ................................ 83 13795

[51] Int. Cl.⁴ ............................................. C07C 68/02
[52] U.S. Cl. ..................... 558/283; 558/281
[58] Field of Search ............................. 260/463

[56] References Cited

U.S. PATENT DOCUMENTS

| | | | |
|---|---|---|---|
| 3,393,270 | 2/1976 | Ekstrom et al. | 514/195 |
| 3,873,521 | 3/1975 | Ekstrom et al. | 260/239.1 |
| 4,426,391 | 1/1984 | Alexander et al. | 260/463 |

FOREIGN PATENT DOCUMENTS

| | | |
|---|---|---|
| 45234 | 2/1982 | European Pat. Off. . |
| 57422 | 8/1982 | European Pat. Off. . |
| 82404 | 6/1983 | European Pat. Off. . |
| 2482587 | 11/1981 | France ............................ 260/463 |
| 1426717 | 3/1976 | United Kingdom . |
| 1598568 | 9/1981 | United Kingdom . |

OTHER PUBLICATIONS

Ebimara et al., *Chemical Abstracts,* vol. 90:87075h (1979).
Hodogaya Chemical, *Chemical Abstracts,* vol. 98:178760j (1983).
Hodogaya Chemical, *Chemical Abstracts,* vol. 97:181747v (1982).
Olofson et al., *J. Org. Chem.,* vol. 49, No. 11, (1984), pp. 2081–2082.
Macko et al., *Chemical Abstracts,* 22706f, 1959.
Muller, *Annalen der Chemie,* 257, pp. 50–67, 1890.

*Primary Examiner*—Donald G. Daus
*Assistant Examiner*—Stephen M. Kapner
*Attorney, Agent, or Firm*—Bucknam and Archer

[57] ABSTRACT

Process for the preparation of α-chlorinated chloroformates with the formula

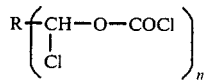

where R is H, an aliphatic or aromatic hydrocarbon radical or heterocyclic radical, substituted or non-substituted and n an integer.

The process consists of reacting $ClCOOCCl_3$ or $Cl_3COCOOCCl_3$ with an aldehyde with formula $R-(CHO)_n$ in the presence of a compound, which in the medium releases a pair of ions, the anion of which being a halide which can attack the aldehyde function, because of the weak attractive power of the cation of this compound.

12 Claims, No Drawings

PROCESS FOR THE PREPARATION OF α-CHLORINATED CHLOROFORMATES

The invention concerns the production of α-chlorinated chloroformates.

For a long time the compounds with the general formula:

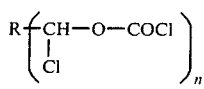

were only prepared by photochemical chlorination of the chloroformates $RCH_2OCOCl$ with simultaneous formation of a large number of secondary derivatives more or less easy to separate from the required product. Recently a new process allowing appreciably pure α-chlorinated derivatives to be obtained, has been described in the French patent applications published under No. 2.482.587 and 2.516.075.

This process is based on the action of phosgene on aldehydes with very different structures, in the presence of a catalyst capable of producing in the reaction medium a pair of ions one of which is a halide and the other a cation sufficiently separated from the said anion to give it a nucleophilic capacity so that it can attack the aldehyde function or functions. This process involves handling large quantities of phosgene which necessitates very specific safety precautions to be taken both in the transport and storage of the reagent as well as in handling it during the reaction. This highly toxic reagent has in fact a particularly high vapour tension at ambient temperatures and above.

It is therefore advisable to have available another general process for preparing α-chlorinated chloroformates which is easier to put into practice, in particular when it comes to the operating conditions and safety conditions.

The process according to the invention can be applied to the preparation of a large number of α-chlorinated chloroformates without it being necessary to operate under the strict safety conditions imposed by the use of phosgene.

The process of the invention concerns the preparation of α-chlorinated chloroformates with the formula:

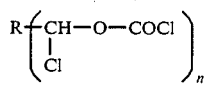

where R represents the hydrogen atom, an aliphatic hydrocarbon radical, in particular C1–C12, an aromatic or heterocyclic radical, substituted or non-substituted and n is an integer, and is characterised by reacting a trichloromethyl derivative chosen from trichloromethyl chloroformate $ClCOOCCl_3$ and di(trichloromethyl) carbonate $Cl_3COCOOCCl_3$ with an aldehyde with formula $R(CHO)_n$, in the presence of a compound capable of liberating in the medium, directly or indirectly, a pair of ions, the anion of which is a halide such that the power of attraction of the cation for the ion of opposite charge is sufficiently weak for the anion to attack the aldehyde function, the cation also tending not to react with the chloroformate functions of the medium.

The reaction may take place with or without a solvent as a third component.

The trichloromethyl derivative used has a vapour tension appreciably lower than that of phosgene and the risks encountered during handling are far less. It may be prepared for example by the process described in Organic Synthesis 59 p 195–201 John WILEY and Sons which involves carrying out a photochemical chlorination of methyl chloroformate or of dimethyl carbonate.

The process according to this invention may be applied to compounds with a single aldehyde function and it is also suitable for compounds with more than one aldehyde function.

As an aldehyde, formaldehyde may be cited which reacts quantitatively if the necessary precautions are taken to prevent its polymerisation. However, acetaldehyde, valeraldehyde, chloral, acrolein and cyclohexylcarboxaldehyde as well as benzaldehyde, 2-chlorobenzaldehyde or terephthalic aldehyde can also be cited. This list is not restrictive. Other heavier or more complex aldehydes can also be used as starting material.

The following compounds may be cited as capable of liberating a pair of suitable ions in the medium: pyridine and alkylpyridines, amides disubstituted on the nitrogen, ureas, tetrasubstituted thioureas and preferably tetrabutylurea and tetramethylurea, phosphoroamides substituted on the nitrogen, including hexamethylphosphotriamide and their products of reaction with chlorinating agents such as the trichloromethyl derivative previously defined.

The quaternary ammonium halides can also be mentioned:

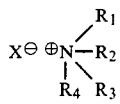

where x represents a halogen, the radicals $R_1$, $R_2$, $R_3$, $R_4$ are hydrocarbon groups where the sum of the carbon atoms is greater than or equal to 16 and preferably such that each group has at least 4 carbon atoms so that the nitrogen carrying the positive charge is sufficiently screened by the bulky substituents in its immediate environment as in tributylbenzylammonium chloride.

A metal halide may also be used with an alkaline or alkaline earth metal where the cation is sequestrated by a crown ether or a cryptant such as the crown ether 18/6 or diaza-1,10-hexaoxa-4,7,13,16,21,24-bicyclo(8,8,8)hexacozane and potassium chloride.

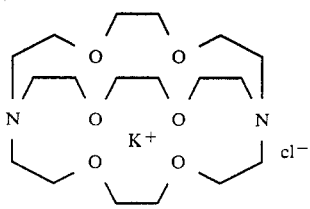

In the above, a halide is understood as a chloride, bromide or iodide, the chloride being preferred.

When putting the process of the invention into practice the amounts of this compound added to the medium will vary according to the nature of the aldehyde used and also according to the nature of the compound.

In general, 0.5–10% mole of the substance will be used with respect to the aldehyde and preferably 2–7%. However, in specific cases it is possible to add up to 50% of the compound without any major drawback.

The reaction according to the invention may be carried out without solvent in particular when the reagents are liquid at the chosen temperature or in an inert solvent, for instance aprotic and non-polar or hardly polar such as chlorinated or non-chlorinated aliphatic hydrocarbons, (carbon tetrachloride, chloroform, methylene chloride or hexane) or aromatic hydrocarbons such as toluene and chlorobenzene. It is important to only use anhydrous solvents free of dissolved hydrochloric acid otherwise the yield of the process may be appreciably reduced. The reaction mixture should be preferably maintained at a temperature lying between $-10°$ C. and $100°$ C. and more particularly between $0°$ and $70°$ C., this temperature being especially a function of the instability of the final product.

The recommended procedure for carrying out the synthesis according to the process of the invention most often consists of mixing the aldehyde and the additional compound releasing the halide anion with or without a solvent as a third component to be cooled if necessary in a reactor shielded from moisture and then adding the trichloromethyl derivative to the medium and finally heating the mixture if necessary to maintain a suitable reaction temperature.

The invention is illustrated by the following examples but it is not limited by them and in particular the process according to the invention may be applied to considerably larger amounts of reagents. The process according to the invention makes it easy to obtain α-chlorinated chloroformates which are used in particular in the production of certain penicillins and cephalosporins in which it is useful to protect the carboxylic acid functions in order to improve the therapeutic properties of the base structure. The α-chlorinated chloroformates can also be used for the selective N-dealkylation of tertiary amines in the morphinane series as described for example in the Journal of Organic Chemistry 1984–49, p. 2081–2082.

EXAMPLE 1

1-chloroethyl chloroformate

The reaction used is as follows:

3.52 g (0.08 mole) acetaldehyde and 1.6 g (0.004 mole) of chlorotetrabutylimonium chloride

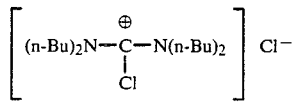

which may be prepared by heating tetrabutylurea and a chlorinating agent such as $POCl_3$, $COCl_2$, $Cl_3COCOCl$ and $Cl_3COCOOCCl_3$ are added to a 50 ml reactor equipped with a stirrer and reflux condenser with a calcium chloride trap.

9.5 g $Cl_3COCOCl$ (0.048 mole) are added drop by drop while stirring for about 20 minutes, keeping the temperature between $20°$ and $30°$ C. The stirring is continued for ½ hour after the addition has been completed.

The reaction mixture is then analysed by infrared spectometry and nuclear magnetic resonance on a sample of one aliquot part. In this way it is confirmed that all of the acetaldehyde has reacted (disappearance of the characteristic quadruplet at 9.7 ppm in the NMR) and has been converted to 1-chloroethyl chloroformate (doublet at 1.85 ppm corresponding to the proton of the $CH_3$ and quadruplet at 6.44 ppm for the proton of the CH in the NMR); the characteristic frequency of the carbonate carbonyl is 1780 $cm^{-1}$.

When the reaction is complete the insoluble substances are separated out and the final product isolated by distillation. Its boiling point is $68°$ C. under 18,950 Pa (150 mm Hg).

EXAMPLE 2

1-chloroethyl chloroformate

The procedure of example 1 is followed but this time the substance added is pyridine.

Thus, 3.1 g (0.07 mole) acetaldehyde, 0.3 g (0.004 mole) pyridine and 8.5 g (0.043 mole) trichloromethyl chloroformate are reacted together. The temperature is maintained for 2 hours between $20°$ and $25°$ C. after the chloroformate has been added. The NMR analysis of the reaction medium at this time indicates that the final product has been formed with a yield of 96.3%.

EXAMPLE 3

1-chloroethyl chloroformate

The procedure of the preceding example is followed but 1.1 g (0.0035 mole) of anhydrous benzyl-tri(n-butyl)ammonium chloride are used instead of pyridine.

The yield as established by NMR is 81.3%.

EXAMPLE 4

1-chloroethyl chloroformate

The procedure of example 3 is followed but with a larger reaction mass.

21.5 g (0.48 mole) acetaldehyde, 7.6 g (0.024 mole) benzyl tri(n-butyl)ammonium and 53 g (0.27 mole) trichloromethyl chloroformate are reacted together. On completion of the reaction, the reaction mixture is distilled under reduced pressure (2660 Pa) to give 60.6 g of a fraction having distilled between $20°$ and $40°$. A second distillation of this fraction under atmospheric pressure gives 52.4 g 1-chloroethyl chloroformate with boiling point $117°$ C. and refractive index $n_D^{20} = 1.4220$. The overall yield is 77%.

EXAMPLE 5

1-chloroethyl chloroformate in the presence of crown ether and potassium chloride The procedure of example 2 is followed but using a mixture of 0.5 g (0.007 mole) potassium chloride and 1 g (0.0004 mole) crown ether 18-6 marketed by MERCK-Darmstadt (West Germany).

The reaction yield determined by NMR is 52.4%.

EXAMPLE 6

α-chlorobenzyl chloroformate 7.5 g (0.07 mole) benzaldehyde and 0.3 g (0.004 mole) pyridine are introduced in an apparatus similar to that of example 1. The mixture is brought to $45°$ C. and 8.5 g (0.043 mole) trichloromethyl chloroformate added drop by drop over 10 minutes. After 2 hours of stirring at 45° it is confirmed by NMR analysis that all the aldehyde has been converted to the α-chlorinated chloroformate with formula:

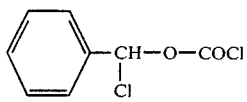

EXAMPLE 7

Chloromethyl chloroformate

The reaction used is the following:

$$2HCHO + Cl_3COCOCl \rightarrow 2ClCH_2OCOCl$$

The procedures are specific to the preparation of this compound because of the particular reactivity of formaldehyde, especially its polymerisation facility.

First 7 g (0.035 mole) trichloromethyl formate and 1.4 g (0.004 mole) anhydrous benzyl tri(n-butyl)ammonium chloride are introduced to an identical apparatus to that of example 1 while cooling the medium to 0° C. and then 2.5 g formaldehyde obtained by heating 2.5 g paraformaldehyde previously dried under a vacuum of 13 Pa in the pressure of $P_2O_5$. The formaldehyde vapour is added to the reaction medium below the surface by means of a submerged tube.

After an hour of stirring at 0° C. it is found by NMR analysis that the reaction is complete (singlet at 5.7 ppm).

We claim:

1. A process for the preparation of an alpha-chlorinated chloroformate of formula:

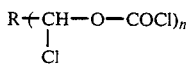

wherein R is hydrogen, saturated or unsaturated, unsubstituted $C_1$-$C_{12}$ aliphatic, cycloaliphatic hydrocarbon radical, or unsubstituted aromatic hydrocarbon radical or R is —$CCl_3$ or the radical from chlorobenzaldehyde and n=1 or 2, which consists of reacting a trichloromethyl derivative which is trichloromethyl chloroformate or di(trichloromethyl)carbonate with an aldehyde of formula $R(CHO)_n$ wherein R and n are as defined hereinabove, in the presence of 2-7% mole with respect to said aldehyde of a compound which is a member selected from the group consisting of pyridine, alkyl pyridines, N,N-disubstituted amides, tetrasubstituted ureas and thioureas, phosphoroamides substituted on the nitrogen and reaction products thereof with a chlorinating agent, quaternary ammonium halides or alkali or alkaline earth metal halides wherein the cation is sequestrated by a crown ether or a cryptand.

2. Process according to claim 1, wherein the reaction is carried out without solvent in an anhydrous medium and in the absence of hydrochloric acid.

3. Process according to claim 1 wherein the reaction is carried out at a temperature between −10° C. and 100° C.

4. Process according to claim 1 wherein the reaction is carried out in a non-polar or weakly polar aprotic solvent in the absence of traces of water and hydrochloric acid.

5. The process according to claim 1 wherein said aldehyde is RCHO in which R is as defined hereinabove.

6. The process according to claim 5 wherein said aldehyde is acetaldehyde, valeraldehyde, chloral, acrolein, cyclohexylcarboxaldehyde, benzaldehyde or 2-chloro-benzaldehyde.

7. The process according to claim 1 wherein said aldehyde is terephthaldehyde.

8. The process according to claim 1 wherein said trichloromethyl derivative is trichloromethyl chloroformate.

9. The process according to claim 3 wherein the temperature is between 0° C. and 70° C.

10. The process according to claim 1 wherein the reaction of said aldehyde and trichloromethyl chloroformate is carried out in the presence of chlorotetrabutyl imonium chloride.

11. A process for the preparation of an alpha-chlorinated chloroformate of formula:

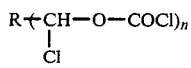

wherein R is hydrogen, saturated or unsaturated, unsubstituted $C_1$-$C_{12}$ aliphatic, cycloaliphatic hydrocarbon radical, or unsubstituted aromatic radical, or R is —$CCl_3$ or the radical from chlorobenzaldehyde and n−1 or 2, which consists of reacting a trichloromethyl derivative which is trichloromethyl chloroformate or di(trichloromethyl)carbonate with an aldehyde of formula $R(CHO)_n$ wherein R and n are as defined hereinabove, in the presence of 2-7% mole with respect to the aldehyde, of a compound which is a quaternary ammonium halide or alkali or alkaline earth metal halide wherein the cation is sequestrated by a crown ether or a cryptand.

12. The process according to claim 11 wherein the quaternary ammonium halide has the formula $X^-N^+(R_1R_3R_3R_4)$ wherein X is halogen and $R_1R_2R_3R_4$ are hydrocarbon radicals, each of $R_1R_2R_3R_4$ has at least four carbon atoms.

* * * * *